(12) United States Patent
Ge

(10) Patent No.: US 8,632,757 B1
(45) Date of Patent: *Jan. 21, 2014

(54) ANTIPERSPIRANT COMPOSITIONS AND METHODS FOR PREPARING ANTIPERSPIRANT COMPOSITIONS

(71) Applicant: The Dial Corporation, Scottsdale, AZ (US)

(72) Inventor: Haiyan Ge, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/686,288

(22) Filed: Nov. 27, 2012

(51) Int. Cl.
*A61K 8/00* (2006.01)

(52) U.S. Cl.
USPC .......................................................... 424/65

(58) Field of Classification Search
None
See application file for complete search history.

(56) References Cited

U.S. PATENT DOCUMENTS

| 6,387,358 B2 * | 5/2002 | Chuah et al. .................... 424/65 |
| 2008/0152608 A1 | 6/2008 | Cropper et al. |

* cited by examiner

*Primary Examiner* — Paul Dickinson
(74) *Attorney, Agent, or Firm* — David K. Benson

(57) ABSTRACT

Antiperspirant compositions are provided. In an exemplary embodiment, an antiperspirant composition includes an active antiperspirant compound and a structurant compound. The structurant compound includes a polyethylene having an average molecular weight of about 450 Daltons to about 580 Daltons and a polydispersity of greater than or equal to about 1.03. The polyethylene has a melting temperature of less than about 82° C.

8 Claims, No Drawings

ANTIPERSPIRANT COMPOSITIONS AND METHODS FOR PREPARING ANTIPERSPIRANT COMPOSITIONS

TECHNICAL FIELD

The present disclosure generally relates to antiperspirant compositions and methods for preparing antiperspirant compositions, and more particularly relates to antiperspirant compositions including a polyethylene structurant and methods for preparing the same.

BACKGROUND

Antiperspirants are popular personal care products used to prevent or eliminate perspiration and body odor caused by perspiration. Antiperspirant products, including for example sticks, emulsions, aerosol sprays, and roll-on antiperspirants are desired by a large majority of the population because of the presence of active antiperspirant compounds that minimize or prevent the secretion of perspiration by blocking or plugging ducts of sweat-secreting glands, such as those located at the underarms. Antiperspirants typically include an active antiperspirant compound in a carrier that permits the antiperspirant product to be applied to the skin by swiping or rubbing the stick across the skin, typically of the underarm. Upon application of the antiperspirant product, the carrier coats the skin or evaporates, releasing the active antiperspirant compound from the antiperspirant product upon exposure to moisture to form plugs in the sweat ducts.

Active antiperspirant compounds reduce underarm wetness and odor by migrating into openings of the sweat gland ducts and reacting with proteins therein to form antiperspirant plugs, which mechanically prevent sweat from escaping the ducts. Two types of sweat glands are present in the underarm region. The first type of sweat gland, the apocrine sweat gland, terminates and secretes at the top of hair follicles. As such, active antiperspirant compounds should migrate into the hair follicle to access the apocrine sweat gland duct and block secretion. The second type of sweat gland, the eccrine sweat gland, opens directly onto the skin. Eccrine sweat is responsible for the largest volume of sweat that causes underarm wetness. As with apocrine sweat glands, active antiperspirant compounds migrate into the eccrine sweat gland openings and form plugs, which reduce underarm wetness.

Some antiperspirant compositions known in the art of the stick type include one or more structurant compounds, which are included to provide good "glide" qualities (i.e., ease of application when the stick is moved across the underarm region) and to minimize residue deposits on the skin. Exemplary structurant compounds currently known in the art include intermediate molecular weight polyethylenes, such as polyethylenes having an average molecular weight between about 360 Daltons and 460 Daltons.

The manufacture of such polyethylene structurants, however, requires the use processing conditions that are undesirable. For example, where the above-noted intermediate molecular weight polyethylenes are employed in an antiperspirant composition, it is necessary to melt the polyethylenes before they can be combined with the active antiperspirant compound. Such melting requires the use of undesirably high processing temperatures in the manufacturing process, such as at least about 85° C., which corresponds with the approximate melting point of these intermediate molecular weight polyethylene compounds.

As is well known in the art, high processing temperatures not only consume high operation energy, but it also increases the risk of corrosion on the manufacturing equipment. For example, certain active antiperspirant compositions increase in acidity with increasing temperature, thereby causing an increased risk of corrosion to the manufacturing equipment. Furthermore, the use of such high operating temperature increases both the complexity and cost of manufacturing the antiperspirant composition by requiring additional heating elements to achieve the higher temperature and additional safety precautions for the personnel operating the equipment.

Accordingly, it is desirable to provide antiperspirant compositions that exhibit the same or similar glide and residue deposition qualities as antiperspirant compositions that intermediate molecular weight polyethylenes, but that do not require excessively high processing temperatures for their manufacture. Further, it is desirable to provide methods for preparing these antiperspirant compositions. Still further, other desirable features and characteristics of the present disclosure will become apparent from the subsequent detailed description the appended claims, taken in conjunction with the accompanying drawings and background.

BRIEF SUMMARY

Antiperspirant compositions and methods for preparing the same are provided. In an exemplary embodiment, an antiperspirant composition includes an active antiperspirant compound and a structurant compound. The structurant compound includes a polyethylene having an average molecular weight of about 450 Daltons to about 580 Daltons and a polydispersity of greater than or equal to about 1.03. The polyethylene has a melting temperature of less than about 82° C.

In another exemplary embodiment, a method for preparing an antiperspirant composition includes combining an active antiperspirant compound, an alcohol, and water at a first temperature to foim a first mixture and combining a structurant compound and a silicone oil at a second temperature to form a second mixture. The structurant compound includes a polyethylene having an average molecular weight of about 450 Daltons to about 580 Daltons and a polydispersity of greater than or equal to about 1.03. The polyethylene has a melting temperature of less than about 82° C. The second temperature is less than about 82° C. The method further includes mixing the first mixture and the second mixture, and then homogenizing the combined first mixture and the second mixture to form the antiperspirant composition. Still further, the method includes pouring the antiperspirant composition into a mold and cooling the mold to a third temperature that is lower than both the first and second temperatures.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosed embodiments or the application and uses of the disclosed embodiments. Furthermore, there is no intention to be bound by any theory presented in the preceding background or the following detailed description.

The various embodiments contemplated herein relate to antiperspirant compositions and methods for preparing antiperspirant compositions. The various embodiments of the compositions exhibit desirable glide and residue deposit characteristics, while avoiding the need for processing at excessively high temperatures, such as 85° C. or above. The various embodiments of the methods described herein provide processing steps for the preparation of such compositions.

Water Phase

Antiperspirant compositions in accordance with the present disclosure include a water phase. The water phase includes water and one or more water-soluble compounds. In an exemplary embodiment, the water phase includes water, an active antiperspirant compound, and a skin emollient to improve the skin "feel" of the antiperspirant composition as it is applied to the skin.

In one embodiment, an antiperspirant composition in accordance with the present disclosure includes a water-soluble active antiperspirant compound in the water phase. Active antiperspirant compounds contain at least one active ingredient, for example metal salts, that, as noted above, are thought to reduce perspiration by diffusing through the sweat ducts of apocrine glands and eccrine glands and hydrolyzing in the sweat ducts, where they combine with proteins to form an amorphous metal hydroxide agglomerate, plugging the sweat ducts so perspiration cannot diffuse to the skin surface.

Some active antiperspirant compounds that may be used in the antiperspirant product include astringent metallic salts, for example inorganic and organic salts of aluminum, zirconium, and zinc, including tetra- and octa-salts, as well as mixtures thereof. Exemplary compounds include aluminum-containing and/or zirconium-containing salts or materials, such as aluminum halides, aluminum chlorohydrates, aluminum hydroxyhalides, zirconyl oxyhalides, zirconyl hydroxyhalides, and mixtures thereof. Exemplary aluminum salts include those having the general formula $Al_2(OH)_aCl_bx(H_2O)$, wherein a is from 2 to about 5; a and b total to about 6; x is from 1 to about 6; and wherein a, b, and x may have non-integer values. Exemplary zirconium salts include those having the general formula $ZrO(OH)_{2-a}Cl_ax(H_2O)$, wherein a is from about 1.5 to about 1.87, x is from about 1 to about 7, and wherein a and x may both have non-integer values. Exemplary zirconium salts are those complexes that additionally contain aluminum and glycine, commonly known as ZAG complexes. These ZAG complexes contain aluminum chlorohydroxide and zirconyl hydroxy chloride conforming to the above-described formulas. Examples of active antiperspirant compounds suitable for use in the various embodiments contemplated herein include aluminum dichlorohydrate, aluminum-zirconium octachlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum-zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, zirconium chlorohydrate, aluminum chloride, aluminum sulfate buffered, and the like, and mixtures thereof. In one embodiment, the active antiperspirant compound is aluminum zirconium pentachlorohydrex glycine complex or aluminum zirconium trichlorohydrex glycine complex.

In an embodiment, the antiperspirant composition includes an active antiperspirant compound in an amount of about 10 wt. % to about 30 wt. % of the overall antiperspirant composition. As used herein, the weight percent or wt. % of the active antiperspirant compound is calculated as an anhydrous weight percent but with bound glycine included in the calculation, as is well known in the art. As such, this calculation excludes any bound water but includes any bound glycine. In an exemplary embodiment, the antiperspirant composition includes about 15 wt. % to about 25 wt. % aluminum zirconium octachlorohydrex glycine complex, for example about 18% aluminum zirconium octachlorohydrex glycine complex.

In to the antiperspirant salt, the antiperspirant composition can include a water-soluble aliphatic alcohol, which may be monohydric or polyhydric. The weight proportion of aliphatic alcohol is typically provided in a weight percentage of less than about 25% of the overall antiperspirant composition, for example less than about 15 wt. %. In one embodiment, the weight percentage of the water-soluble aliphatic alcohol is less than about 10%, for example less than about 5%. Used as a humectant to enhance skin feel, in some embodiments, the alcohol can be, for example, propylene glycol. An exemplary antiperspirant composition includes less than about 15 wt. % propylene glycol, for example about 8 wt. % propylene glycol.

As noted above, the water phase also includes water. Water is provided to solubilize the water phase components of the antiperspirant composition, such as the active antiperspirant compound and the alcohol described above, in addition to any other water soluble components that may be present in the water phase. In one embodiment, water is provided in a weight percentage of the overall antiperspirant composition from about 20% to about 60%, such as from about 30% to about 50%, for example about 40%.

To prepare the water phase, the components thereof, for example the water, the active antiperspirant compound, and the alcohol are combined and heated. For example, the components can be combined and heated to a temperature of about 65° C., 70° C., or 75° C., or any temperature thereinbetween. Further, the components of the water phase can be mechanically agitated to promote solubilization, such as by moderate stirring. As such, the water phase, when combined, includes about 60 wt. % to about 75 wt. % of the overall antiperspirant composition, such as about 60 wt. % to about 70 wt. %, for example about 64 wt. %.

Oil Phase

Antiperspirant compositions according to the present disclosure are formulated as a water-in-oil emulsion. As such, in addition to the water phase described above, the antiperspirant compositions also include an oil phase. In an exemplary embodiment, the oil phase includes one or more structurants, one or more carrier solvents, and one or more emulsifiers/surfactants/co-surfactants.

As such, in one embodiment, an antiperspirant composition in accordance with the present disclosure includes at least one polyethylene structurant in the oil phase, which as noted above facilitates the solid consistency of the antiperspirant stick product, in additional to providing desirable glide qualities and minimized residue deposited on the skin. As is known in the art, polyethylene structurant compounds can be provided as mixtures having polyethylenes within a wide range of molecular weights. As such, polyethylene structurants are typically described with reference to an average molecular weight, i.e., a mass average of all of the constituent polyethylene molecules in the structurant. As will be discussed in greater detail below, in an exemplary embodiment, the polyethylene is selected as having an average molecular weight from about 360 Daltons to about 600 Daltons, for example from about 450 Daltons to about 580 Daltons, or a mixture of such polyethylenes.

As is further known in the art, polyethylene structurant may also be described with reference to a polydispersity index. The polydispersity index (PDI) or heterogeneity index, is a measure of the distribution of molecular mass in a given polymer sample. The PDI calculated is the weight average molecular weight $M_w$ divided by the number average molecular weight $M_n$. The PDI indicates the distribution of individual molecular masses in a batch of polymers. The PDI has a value equal to or greater than 1, but as the polymer chains approach uniform chain length, the PDI approaches unity. As will be discussed in greater detail below, the polyethylene is selected having a PDI equal to or greater than about 1.03, such as greater than about 1.05.

In one embodiment, the polyethylene compound is provided in a weight percentage of about 5 wt. % to about 15 wt. % of the overall antiperspirant composition, for example about 10 wt. %, about 11 wt. %, or about 12 wt. %. Desirably, the polyethylene compound is present in a proportion high enough to solidify the emulsion and provide a hardness sufficient for preparation as a stick antiperspirant.

As noted above, the polyethylene structure is provided with an average molecular weight from about 450 Daltons to about 580 Daltons, and with a PDI of greater than or equal to about 1.03, such as greater than or equal to about 1.05. The inventors have surprising discovered that this combination of structurant qualities, when combined into an antiperspirant formulation as described herein, provide desirable hardness for preparation as a stick antiperspirant while allowing for manufacturing and processing temperatures well below those currently known in the art, for example about 2-3° C. lower than those currently known in the art. For example, in accordance with the present disclosure, and as described in greater detail below, the antiperspirant compositions can be processed and manufactured at maximum temperatures between about 80° C. and about 82° C.

For example, in one embodiment, the polyethylene compound known as Jeenate 3H™, available from Jeen International Corp. of Fairfield, N.J., is used as the structurant for the antiperspirant composition. Jeenate 3H™ desirably has an average molecular weight of about 485 Daltons, a PDI of about 1.052, and a melting point of about 73° C. (melting begins at about 70° C., and melting is complete at about 75° C.). In an exemplary embodiment, Jeenate 3H™ is provided as a polyethylene structurant in the oil phase at a weight percentage of about 10% to about 12%, for example about 11%.

In this embodiment, the polyethylene compound Jeenate 4H™, also available from Jeen International Corp. of Fairfield, N.J., is used as the structurant for the antiperspirant composition in combination with the Jeenate 3H™. Jeenate 4H™ has an average molecular weight of about 571 Daltons, a PDI of about 1.059, and a melting point of about 78° C. Because it is a heavier polyethylene compound, it desirably forms a stick antiperspirant that is harder than Jeenate 3H™. However, because it has a higher melting point, it is desirable to combine the Jeenate 4H™ with the Jeenate 3H™ to achieve an antiperspirant composition that is harder than is achieved with Jeenate 3H™ also, but still retains a desirably low melting point for the reasons discussed above. As such, the inventors have surprisingly discovered that a structurant including Jeenate 4H™ and Jeenate 3H™ in a ratio (3H/4H) of about 3 to about 10, or preferable about 4 to about 10, achieves a desirably hard stick antiperspirant, while allowing for processing and manufacturing temperatures at or below 82° C.

In addition to the above-noted structurant, some embodiments of the antiperspirant compositions described herein further include a relatively small amount (e.g., less than 1% by weight of the overall composition) of a supplemental structurant to improve the hardness of the stick antiperspirant. For example, a suitable supplemental structurant is the synthetic wax sold under the trade name Performa V 343™, available from Baker Hughes Incorporated of Sugar Land, Tex. In one embodiment, such supplemental structurant is provided in a weight percentage of about 0.01% to about 0.5 percent, such as about 0.1%.

In one embodiment, the antiperspirant composition further includes a carrier solvent, such as a hydrophobic carrier solvent, in the oil phase. Exemplary hydrophobic carriers include liquid siloxanes and particularly volatile polyorganosiloxanes, that is, liquid materials having a measurable vapor pressure at ambient conditions. The polyorganosiloxanes can be linear or cyclic or mixtures thereof. The linear volatile silicones generally have viscosities of less than about 5 centistokes at 25° C., while the cyclic volatile silicones have viscosities under 10 centistokes. Exemplary siloxanes include cyclomethicones, which have from about 3 to about 6 silicon atoms, such as cyclotetramethicone, cyclopentamethicone, and cyclohexamethicone, cyclohexasiloxane, and mixtures thereof. The carrier also may include, additionally or alternatively, nonvolatile silicones such as dimethicone and dimethicone copolyols, which have from about 2 to about 9 silicon atoms. Examples of suitable dimethicone and dimethicone copolyols include polyalkyl siloxanes, polyalkylaryl siloxanes, and polyether siloxane copolymers.

The carrier solvent of the oil phase is provided from about 5 wt. % to about 15 wt. % of the overall composition. For example, the carrier solvent can be provided from about 11 wt. % to about 12 wt. %. In an exemplary embodiment, the carrier solvent is cyclohexasiloxane provide at about 7 wt. % or about 8 wt. %. A suitable cyclohexasiloxane is available form Dow Corning Corporation of Midland, Mich. under the trade name PMX-246®.

In addition to the above-noted carrier solvents, an additional high-refractive index carrier solvent may be provided that desirably reduces the appearance of the antiperspirant composition when applied to the skin. Suitable high-refractive index carrier solvents include PPG-14 and aromatic esters, for example. Many of the aromatic esters are benzoate esters, others are naphthylate esters and still others are salicylate esters. Amongst the class of benzoate esters, it is desirable to mention alkyl benzoate, alkylene dibenzoate, alkoxylated alkyl benzoate or a polyalkylene oxide dibenzoate, or a mixture of two or more sub-classes thereof. The alkyl group often contains at least 10 carbons, in many instances up to 25 carbons. It is often linear, but can alternatively be branched. Especially desirable alkyl groups are found in the range of from 12 to 20 carbons and include dodecyl (lauryl) terdecyl, tetradecyl (myristyl), pentadecy, hexadecyl (palmityl), octadecyl (stearyl) 2-methyl-heptadecyl (iso-stearyl) and octyldodecyl groups. A mixture of two or more of the alkyl groups can be employed, such as a mixture of $C_{12}$-$C_{15}$ alkyl groups. The term alkylated herein includes alkylene groups and the latter are terminated at each end with a benzoate group. The alkylene group often contains from 2 to 6 carbons and can be linear or branched, a suitable example of linear being propylene. In the alkoxylated alkyl benzoates contemplated herein, the alkyl group is terminated by an alkoxy group, which can be monomeric containing for example up to 6 carbons or polymeric such as polyethylene oxide or preferably polypropylene oxide, which includes up to 30 units and often from 5 to 20 units. In such compounds, the alkyl group can be selected from the previously identified alkyl groups. Alternatively, the benzoate compound can include a polyethylene oxide or polypropylene oxide moiety, or a block copolymer of ethylene oxide and propylene oxide, terminated at each end by a benzoate group. Mixtures of two or more of the benzoate sub-classes of compounds can be employed.

The above-noted high-refractive index solvents are provided in the antiperspirant composition in a weight percentage from about 5% to about 15%, for example about 10%. In one embodiment, the high-refractive index solvent is provided as a $C_{12}$-$C_{15}$ alkyl benzoate in an amount of about 10 wt. % of the overall composition. Several such benzoate compounds, such as Finsolv TN™, are available from Innospec Incorporated of Lone Tree, Colo.

In one embodiment, the antiperspirant compositions further include at least one water-in-oil emulsifier/surfactant in the oil phase, such as a silicone-based water-in-oil emulsifier. One group of silicone-based water-in-oil emulsifiers which is suitable for use in the presently described compositions are poly-($C_2$-$C_3$)alkylene glycol-modified silicones, the former INCI name of which was dimethicone copolyol, with the current INCI name PEG-x dimethicone (with x=2-20, for example 3-17, such as 11-12), bis-PEG-y dimethicone (with y=3-25, preferably 4-20), PEG/PPG-a/b dimethicone (wherein a and b mutually independently denote numbers from 2-30, for example 3-30, such as 14-18), bis-PEG/PPG-c/d dimethicone (wherein c and d mutually independently denote numbers from 10-25, for example 14-20, such as 14-16), and bis-PEG/PPG-e/f PEG/PPG-g/h dimethicone (wherein e, f, g and h mutually independently denote numbers from 10-20, for example 14-18, such as particularly preferably 16). Further silicone-based W/O emulsifiers may be employed in accordance with the present disclosure are poly-($C_2$-$C_3$)-alkylene glycol-modified silicones, which are hydrophobically modified with $C_4$-$C_{18}$ alkyl groups, for example cetyl PEG/PPG-10/1 dimethicone, alkyl methicone copolyols, and alkyl dimethicone ethoxy glucoside.

In some embodiments, the antiperspirant composition may further include a supplemental emulsifier or co-surfactant. The supplemental emulsifier or co-surfactant is provided to enhance the stability of the emulsion and to reduce the stickiness of the product after application, so as to avoid phase separation prior to application on to the skin. In one example, a suitable co-surfactant is provided as bis-PEG/PPG-14/14 dimethicone in an overall weight percentage of the antiperspirant composition of about 0.05% to about 2%. A suitable bis-PEG/PPG-14/14 dimethicone is available from Evonik Industries AG of Essen, Germany under the trade name Abil EM 97 S™.

The W/O emulsifiers are typically provided in a weight percentage of less than about 5 wt. % of the overall composition, for example less than about 3%, such as less than about 2%. In an exemplary embodiment, the W/O emulsifier is cetyl PEG/PPG-10/1 dimethicone provided in a weight percentage of less than about 2%, for example about 1.5%. A suitable cetyl PEG/PPG-10/1 dimethicone is available from Evonik Industries AG of Essen, Germany under the trade name Abil EM 90™. As a co-emulsifier, a suitable bis-PEG/PPG-14/14 dimethicone is also available from Evonik Industries under the trade name Abil 97S™. A ratio between these two dimethicones copolyol (90/97S) is suitable at about 1 to about 8, or preferable about 2 to about 5. In a preferred embodiment, the HLB value of the emulsifiers is about 3 to about 7, such as about 5 to about 6. The Abil 90/97S products merely serve as examples of such emulsifiers, and others will be known to those having ordinary skill in the art.

In addition to the compounds identified above, the antiperspirant product may optionally include additives, such as those used in conventional antiperspirants. These additives include, but are not limited to, fragrances, including encapsulated fragrances, dyes, pigments, preservatives, antioxidants, moisturizers, and the like. These ingredients can be included in the antiperspirant composition in an amount of about 0 wt. % to about 20 wt. %. In an exemplary embodiment, a fragrance is provided in the antiperspirant composition in a weight percentage of less than about 2%, and is added to the combined phase before homogenization.

To prepare the oil phase, the components thereof, for example the carrier solvents, the structurants, and the emulsifiers/surfactants, are combined and heated to form a single phase mixture. For example, the components can be combined and heated to a maximum temperature of about 80° C. to about 82° C. As noted above, due to the careful selection of structurants and other compounds of the oil phase, heating thereof is desirably performed at a temperature that is significantly lower than had previously been known in the art for antiperspirant compounds including intermediate molecular weight polyethylene structurants. Further, the components of the oil phase can be mechanically agitated to promote integration, such as by moderate stirring. As such, the oil phase, when combined, includes about 25 wt. % to about 40 wt. % of the overall antiperspirant composition, such as about 30 wt. % to about 38 wt. %.

Emulsion

The antiperspirant composition, in an exemplary embodiment, is prepared by combining the water phase, which includes the antiperspirant compound, the alcohol, and water with the oil phase, which includes the structurant, the emulsifying compounds, and the hydrophobic carrier solvent compounds. Any suitable form of mixing can be used to combine (homogenize) the ingredients, such as high shear mixing, stirring, agitation, blending, or any combination thereof. Typically, the water phase is slowly added to the oil phase at a temperature of about 75° C. while continuously stirring to promote thorough homogenization. Thereafter, fragrance may be added, followed by homogenization in a homogenizer.

The final mixture is poured into molds, and then allowed to cool to room temperature, for a time period of, for example 24 hours. As used herein, the term "allowed to cool" means exposing the mixture to room temperature for a time sufficient for the mixture to come to room temperature or exposing the mixture to a refrigerator or cooling room, fan, or other cooling mechanism that lowers the temperature of the mixture to room temperature. It will be appreciated that the sequence of addition and/or combination of the various components of the antiperspirant product is not necessarily critical, and various sequences for addition or combination of the components can be used.

As such, according to an exemplary procedure, a first step includes combining an active antiperspirant compound, an alcohol, and water at a first temperature to form a first mixture. A second step includes combining a structurant compound, a silicone oil, and an emulsifier at a second temperature to form a second mixture, wherein the structurant compound comprises a polyethylene having an average molecular weight of about 450 Daltons to about 580 Daltons and a polydispersity of greater than or equal to about 1.03, wherein the polyethylene has a melting temperature of less than about 82° C., and wherein the second temperature is about 82° C. or less. A third step includes mixing the first mixture and the second mixture using a mixing blade. A fourth step includes homogenizing the first mixture and the second mixture using a homogenizer to form the antiperspirant composition. Further, a fifth step includes pouring the antiperspirant composition into a mold and cooling the mold to a third temperature that is lower than both the first and second temperatures.

The foregoing description has set forth various emulsifiers, co-emulsifiers, and structurants suitable for use in embodiments of the present disclosure. In a preferred embodiment, the total amount of the emulsifiers is about 0.8% to about 1.2%, such as about 1.0% to about 1.2%, of the overall composition by weight. In a preferred embodiment, the ratio of emulsifier to co-emulsifier (such as the ratio of Abil EM 90™/Abil EM 97S™, in one particular example) is about 1 to about 8, such as about 2 to about 5. In a preferred embodiment, the total amount of structurant is about 8% to about 14%, such as about 11% to about 12.5%, of the overall composition by weight. Regarding the ratio of the various structurants, in a preferred embodiment, the ratio of Jeenate 3H™ to Jeenate 4H™ is about 3 to about 10, such as about 4 to about 10. Still further, in a preferred embodiment, the total amount of the water phase is about 63% to about 75%, such as about 63% to about 70%, of the overall composition by weight.

EXAMPLES

The following is an exemplary embodiment of an antiperspirant composition contemplated herein, with each of the components set forth in weight percent of the antiperspirant product. The example is provided for illustration purposes only and is not meant to limit the various embodiments of the antiperspirant product in any way.

Example 1

| Ingredient | Wt. % |
|---|---|
| Water Phase: | |
| Aluminum Zirconium Octachlorohydrex | 59.7 |
| Propylene Glycol | 4.3 |
| Oil Phase: | |
| Cyclohexasiloxane | 11.1 |
| C$_{12}$-C$_{15}$ Alkyl Benzoate | 9.5 |
| Cetyl PEG/PPG-10/1-Dimethicone | 1.0 |
| Bis-PEG/PPG-14/14 Dimethicone | 0.2 |
| Jeenate 3H ™ (Jeen Int'l Corp.)-485 Avg. MW Polyethylene | 10.9 |
| Jeenate 4H ™ (Jeen Int'l Corp/)-441 Avg. MW Polyethylene | 1.2 |
| Performa V 343 ™ Polymer (Baker Hughes Inc.) | 0.1 |
| Additives: | |
| Fragrance | 2.0 |
| Total | 100.0 | wherein Jeenate 3H™ and 4H™ are available from Jeen International Corporation of Fairfield, N.J. and wherein Performa V 343™ Polymer is available from Baker Hughes Incorporated of Sugar Land, Tex.

After the above-noted composition was prepared and then allowed to cool and solidify for several hours, a stick hardness test was performed. A force of 133.85 g's was measured. It was further noted that the solidified composition appeared opaque, and not soft or "mushy." Further force measurements were taken over a period of 3 months, and are set forth in Table 1, below.

TABLE 1

| Hardness (g force) | 1 month | 2 month | 3 month |
|---|---|---|---|
| 4C | 119.90 | 102.65 | 117.70 |
| 25C | 118.00 | 114.25 | 114.40 |
| 40C | 118.65 | 136.95 | 136.20 |

Initial hardness: 133.85

Accordingly, various embodiments of an antiperspirant composition exhibiting desirable glide and residue deposit characteristics have been disclosed. The antiperspirant compositions are desirably processed and manufactured at temperatures significantly less than previously known in the art for antiperspirant compositions including an intermediate molecular weight structurant, and as such exhibit the benefits of lower manufacturing costs, reduced manufacturing equipment wear, and reduced operational complexity. Various embodiments of methods for manufacturing the same have also been provided.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the antiperspirant compounds in any way. Rather, the foregoing detailed description will provide those skilled in the art with a convenient road map for implementing an exemplary embodiment, it being understood that various changes may be made in the elements described in an exemplary embodiment without departing from the scope of the invention as set forth in the appended claims and their legal equivalents.

What is claimed is:

1. An antiperspirant composition comprising:
a homogenized water phase and oil phase, wherein the water phase comprises an active antiperspirant compound, an alcohol, and water, and wherein the oil phases comprises a structurant, a W/O emulsifier, and a hydrophobic carrier solvent,
wherein the structurant compound comprises a polyethylene having an average molecular weight of about 450 Daltons to about 580 Daltons and a polydispersity index of about 1.05, and wherein the polyethylene has a melting temperature of less than or equal to 82° C.

2. The antiperspirant composition of claim 1, wherein the active antiperspirant compound comprises aluminum zirconium octachlorohydrex, tetrachlorohydrex, trichlorohydrex, or pentachlorohydrex, or aluminum chlorohydrates, optionally including a glycine component.

3. The antiperspirant composition of claim 1, wherein the active antiperspirant compound is present in the composition in a weight percentage of about 10% to about 20%.

4. The antiperspirant composition of claim 1, wherein the structurant compound comprises a polyethylene having an average molecular weight of about 485 Daltons and a polyethylene having an average molecular weight of about 571 Daltons.

5. The antiperspirant composition of claim 1, wherein the structurant compound is present in the composition in a weight percentage of about 5% to about 15%.

6. The antiperspirant composition of claim 1, wherein the antiperspirant composition exhibits a stick hardness of greater than 130 g's after preparation.

7. The antiperspirant composition of claim 1, further comprising an additive compound.

8. The antiperspirant composition of claim 7, wherein the additive compound is a fragrance.

* * * * *